US007651077B1

(12) United States Patent
Rosener et al.

(10) Patent No.: US 7,651,077 B1
(45) Date of Patent: Jan. 26, 2010

(54) RELEASING FRAGRANCES INTO THE AIR

(75) Inventors: Martin J. Rosener, Fort Mill, SC (US);
Robert D. Blaylock, Tega Cay, SC (US);
David L. Van Epps, Charlotte, NC (US)

(73) Assignee: ScentAir Technologies, Inc., Charlotte, NC (US)

( * ) Notice: Subject to any disclaimer, the term of this patent is extended or adjusted under 35 U.S.C. 154(b) by 517 days.

(21) Appl. No.: 11/277,021

(22) Filed: Mar. 20, 2006

Related U.S. Application Data

(60) Provisional application No. 60/662,919, filed on Mar. 18, 2005.

(51) Int. Cl.
*B01F 3/04* (2006.01)
(52) U.S. Cl. ............... 261/104; 261/DIG. 88; 239/55; 239/56
(58) Field of Classification Search ......... 261/104, 261/107, DIG. 65, DIG. 88, DIG. 89; 239/45, 239/53, 55, 56
See application file for complete search history.

(56) References Cited

U.S. PATENT DOCUMENTS

| | | | | |
|---|---|---|---|---|
| 2,085,390 A | * | 6/1937 | Quinlivan | 261/104 |
| 2,540,144 A | | 2/1951 | Stern | |
| 2,562,959 A | | 8/1951 | Stern | |
| 2,562,960 A | | 8/1951 | Stern | |
| 2,813,452 A | | 11/1957 | Laube | |
| 2,905,049 A | | 9/1959 | Laube | |
| 3,138,009 A | * | 6/1964 | McCreight | 62/315 |
| 3,628,829 A | | 12/1971 | Hellig | |
| 3,685,734 A | * | 8/1972 | Paciorek et al. | 239/56 |
| 3,795,438 A | | 3/1974 | Westenholz et al. | |
| 4,059,422 A | * | 11/1977 | Steiner | 96/147 |
| 4,065,261 A | * | 12/1977 | Fukada | 261/95 |
| 4,110,419 A | * | 8/1978 | Miller | 261/142 |
| 4,310,307 A | | 1/1982 | Bellisario | |
| 4,603,030 A | | 7/1986 | McCarthy | |
| 4,874,129 A | * | 10/1989 | DiSapio et al. | 239/36 |
| 4,952,024 A | | 8/1990 | Gale | |
| 5,071,704 A | * | 12/1991 | Fischel-Ghodsian | 428/354 |
| 5,273,689 A | * | 12/1993 | Hamasaki | 261/104 |
| 5,610,674 A | | 3/1997 | Martin | |
| 5,713,971 A | * | 2/1998 | Rohrbach et al. | 96/181 |
| 5,732,317 A | * | 3/1998 | Orchard et al. | 399/325 |
| 5,898,475 A | | 4/1999 | Martin | |
| 2002/0054273 A1 | | 5/2002 | Martin | |

OTHER PUBLICATIONS

Petrucci, Ralph H. and Harwood, William S., *General Chemistry*, Seventh Edition, Prentice Hall, 1997, pp. 420-422.

* cited by examiner

*Primary Examiner*—Scott Bushey
(74) *Attorney, Agent, or Firm*—Fish & Richardson P.C.

(57) ABSTRACT

A canister assembly includes a canister body, an inner wick positioned within the canister body and configured to define an air passage, and an outer wick. At least a portion of the outer wick is positioned between the inner wick and the canister body. The inner wick and the outer wick are oriented to enable a transfer of fragrance material to the inner wick from the outer wick. The fragrance material includes fragrance molecules, and the inner wick is configured to enable a transfer of some of the fragrance molecules into air within the air passage.

17 Claims, 9 Drawing Sheets

RELEASING FRAGRANCES INTO THE AIR

CROSS-REFERENCE TO RELATED APPLICATION

The present application claims priority from U.S. provisional application No. 60/662,919 filed Mar. 18, 2005, and titled "A Mechanism for Releasing Fragrances into the Air," the entire contents of which is incorporated herein by reference.

TECHNICAL FIELD

This description relates to releasing fragrances into the air.

BACKGROUND

Mechanisms for releasing fragrances into the air may be used to release fragrance into a room or other space. A liquid scent dispenser may include a cartridge holding a liquid scent.

SUMMARY

According to a general aspect, a canister assembly includes a canister body, an inner wick positioned within the canister body and configured to define an air passage, and an outer wick. At least a portion of the outer wick is positioned between the inner wick and the canister body. The inner wick and the outer wick are oriented to enable a transfer of fragrance material to the inner wick from the outer wick. The fragrance material includes fragrance molecules, and the inner wick is configured to enable a transfer of some of the fragrance molecules into air within the air passage.

Implementations may include one or more of the following features. The fragrance material may include or be fragrance oil. The outer wick may have a greater tendency to transfer fragrance material than the inner wick. The inner wick and the outer wick may be composed of different materials. For example, the inner wick may be composed of blotter paper, and the outer wick may be composed of felt. The inner wick and the outer wick may form substantially concentric cylinders.

The outer wick may have an outer surface, and the canister assembly may include a wrapper. At least a portion of the wrapper may be positioned between the outer wick and the canister body. The wrapper may encase at least a portion of the outer surface of the outer wick. The canister assembly also may include a lip. The lip may interact with the wrapper to form a seal between the wrapper and an inner surface of the inner wick. The lip may collect excess fragrance material.

The inner wick and the outer wick may form an integrated wick such that the inner wick forms an inner portion of the integrated wick while the outer wick forms an outer portion of the integrated wick. The outer portion of the integrated wick may be more porous than the inner portion of the integrated wick. The integrated wick may be a single piece of porous plastic configured such that an outer portion of the porous plastic is more porous than an inner portion of the porous plastic.

According to another general aspect, a fragrance releasing apparatus includes a canister and a fan assembly. The canister includes at least one wicking structure. The wicking structure has an inner surface that defines a canister air channel. The wicking structure is configured to enable a transfer of fragrance molecules into air within the canister air channel. The fan assembly includes fan blades and a fan housing and the fan assembly is oriented to encourage airflow in the canister air channel.

Implementations may include one or more of the features noted above and one or more of the following features. The fan blades may be substantially aligned with the inner surface of the wicking structure. In addition, the fragrance releasing apparatus may include a canister housing for housing the canister. The canister may be replaceable. The fan assembly may be integrated within the canister or the fan assembly may be coupled to the canister.

The wicking structure may be configured to absorb fragrance material, and the fragrance material may include fragrance molecules. Air contacting the inner surface of the wicking structure may enable the transfer of fragrance molecules into air within the canister air channel.

The fragrance releasing apparatus may include a second wicking structure that is positioned between the first wicking structure and an inner surface of the canister. The second wicking structure may have an outer surface, and the canister may include a wrapper. At least a portion of the wrapper may be positioned between the second wicking structure and the inner surface of the canister. The wrapper may encase at least a portion of the outer surface of the second wicking structure. The wrapper may be composed of a polyester film. The fragrance releasing apparatus also may include a lip. The lip may interact with the wrapper to form a seal between the wrapper and the inner surface of the first wicking structure.

The fragrance releasing apparatus also may include canister air channel dividers. The canister air channel dividers may be positioned within the canister air channel. In addition, the air channel dividers and the wicking structure may be composed of the same material.

The fragrance releasing apparatus may include a sensor operable to detect a predetermined condition and to trigger operation of the fan assembly in response to detection of the predetermined condition. For example, the fragrance releasing apparatus may include a motion sensor operable to detect motion within the vicinity of the fragrance releasing apparatus. Detection of motion within the vicinity of the fragrance releasing apparatus may trigger the operation of the fan assembly. The sensor may be a light sensor, a heat sensor, a tactile sensor, a haptic sensor, or an ultrasonic sensor.

According to yet another general aspect, a canister for releasing fragrance material is assembled. The canister includes an inner wick that defines an air channel, an outer wick, a fan, and a canister body. The outer wick is configured to absorb the fragrance material and to transfer the fragrance material to the inner wick. The inner wick is configured to enable a transfer of some of the fragrance molecules into air within the air channel. In order to assemble the canister, fragrance material, including fragrance molecules, is applied to the outer wick. In addition, the inner wick is positioned within the canister body and the outer wick is positioned between the inner wick and the canister body. The inner wick and the outer wick are oriented to enable a transfer of fragrance material to the inner wick from the outer wick. Additionally, a fan is coupled to the canister body and the fan is oriented so as to encourage airflow through the air channel.

Implementations may include wrapping the outer wick with a wrapper so as to form a barrier between the outer wick and air.

The details of one or more implementations are set forth in the accompanying drawings and the description below. Other features will be apparent from the description and drawings, and from the claims.

DESCRIPTION OF DRAWINGS

Like reference symbols in the various drawings indicate like elements.

DETAILED DESCRIPTION

An apparatus for releasing fragrances into the air includes a fragrance dispensing canister assembly housed within a canister housing. The fragrance dispensing canister assembly includes a wicking structure impregnated with fragrance material. Fragrance material also may be referred to as fragrant material or scent material. Airflow through the fragrance dispensing canister is encouraged such that molecules of the fragrance material are evaporated into the air flowing through the fragrance dispensing canister. As such, the mechanism for releasing fragrances into the air may be used to deliver a fragrance to a room or other space. Some implementations of the apparatus may be capable of effectively delivering fragrance to a relatively large area including, for example, commercial or industrial environments.

Figure 1:
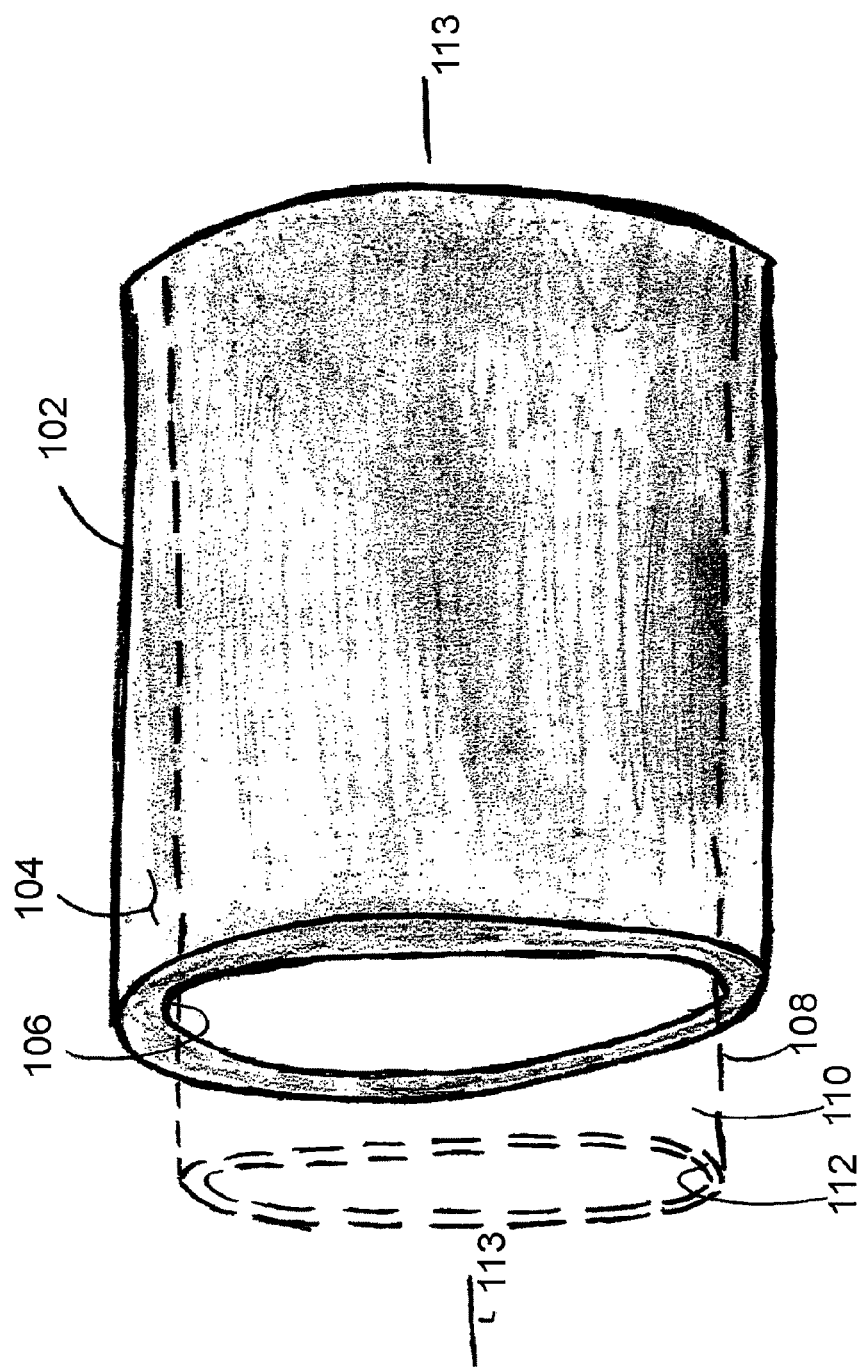
FIG. 1 is an illustration of a wicking structure.

Referring to FIG. 1, a wicking structure 100 includes a cylindrical outer wick 102 having an outer surface 104 and an inner surface 106 and a cylindrical inner wick 108 having an outer surface 110 and an inner surface 112. The inner wick 108 is positioned within the outer wick 102 such that the inner wick 108 and the outer wick 102 form concentric cylinders about an axis 113. The inner surface 112 of the inner wick 108 defines an air channel for channeling air through the interior of the wicking structure 100. The wicking structure 100 is configured to absorb fragrance material, for example, fragrance oil, and to facilitate the transfer (e.g., evaporation) of molecules of the fragrance material into air occupying or flowing through the air channel. The wicking structure 100 may serve multiple purposes. For example, the wicking structure 100 may function as both a reservoir for fragrance material and as a mechanism for transferring fragrance material into the air.

In the example of FIG. 1 where the fragrance material is fragrance oil, the fragrance oil is applied to the outer wick 102. Fragrance oil also may be referred to as fragrant oil or scent oil. The outer wick 102 absorbs the applied fragrance oil such that the fragrance oil is suspended within the outer wick 102.

As the fragrance oil is absorbed by the outer wick 102, the fragrance oil has a tendency to migrate across the outer wick 102 until the fragrance oil is evenly distributed throughout the outer wick 102. The outer wick 102 will continue to absorb fragrance oil, and consequently fragrance oil will continue to migrate across the outer wick 102, until the outer wick 102 is completely saturated. The migration of the fragrance oil across the outer wick 102 may be accomplished by, or at least facilitated by, capillary action within the outer wick 102.

The outer wick 102 is configured to feed fragrance oil to the inner wick 108, and the inner wick 108 is positioned so as to enable the transfer of fragrance oil from the inner surface 106 of the outer wick 102 to the outer surface 110 of the inner wick 108. For example, the outer surface 110 of the inner wick 108 may contact the inner surface 106 of the outer wick 102. Consequently, fragrance oil suspended within the outer wick 102 migrates from the outer wick 102 into the inner wick 108 until fragrance oil is evenly distributed throughout both the outer wick 102 and the inner wick 108. The concentric cylinder configuration of the outer wick 102 and the inner wick 108 may facilitate a substantially uniform transfer of fragrance oil from the outer wick 102 across the circumference of the inner wick 108. In addition, the migration of the fragrance oil across the inner wick 108 may be accomplished by, or at least facilitated by, capillary action within the inner wick 108.

Fragrance oil that migrates to the inner surface 112 of the inner wick 108 is exposed to air occupying or flowing through the air channel and, as a result, some of the molecules of fragrance oil are evaporated. The evaporation of fragrance molecules from the inner surface 112 of the inner wick 108 reduces the concentration of fragrance oil in the vicinity of the inner surface 112 of the inner wick 108. As a result, the evaporated fragrance oil is replenished by fragrance oil that migrates to the inner surface 112 of the inner wick 108 so as to maintain an even distribution of fragrance oil throughout both the outer wick 102 and the inner wick 108.

By absorbing fragrance oil and subsequently transferring the absorbed fragrance oil to the inner wick 108, the outer wick 102 effectively functions as a reservoir for storing fragrance oil before the fragrance oil is transferred to the inner wick 108 where the fragrance oil is evaporated into the air. As compared to storing the fragrance oil in a well-like reservoir structure, suspending the fragrance oil within the outer wick before the fragrance oil is transferred to the inner wick 108 to be evaporated may allow the wicking structure to be oriented in various positions with diminished risk of leakage or spillage of the fragrance oil. In addition, the fact that the outer wick 102 may uniformly transfer fragrance oil across the circumference of the inner wick 108 may reduce the overall distance across which the fragrance oil must migrate before being exposed to air for evaporation vis-à-vis a wicking structure that draws fragrance oil from a well-like reservoir structure.

The thickness of the inner wick 103 may be substantially uniform. Alternatively, the inner wick 108 may be configured such that the thickness of the inner wick 108 is not uniform. For example, the inner wick 108 may be configured so as to form fins or other topological features on the inner surface 112 of the inner wick 108 in order to increase the surface area available for exposing fragrance oil to air, thereby increasing the quantity of fragrance oil exposed to air within the air channel.

The dimensions (e.g., length, circumference, and/or thickness) of the outer wick 102 and the inner wick 108 may be modified with respect to one another in order to realize relative differences in the capacity of wicking structure 100 for absorbing fragrance oil and/or to realize relative differences in the amount of fragrance oil released by the wicking structure 100. Generally, the larger the volume of the wicking structure 100, the greater the amount of fragrance oil the wicking structure is able to absorb. Similarly, increasing the surface area of the inner surface 112 of the inner wick 108 generally increases the amount of fragrance oil exposed to the air and therefore helps to increase the amount of fragrance oil released by the wicking structure 100.

Figure 2:
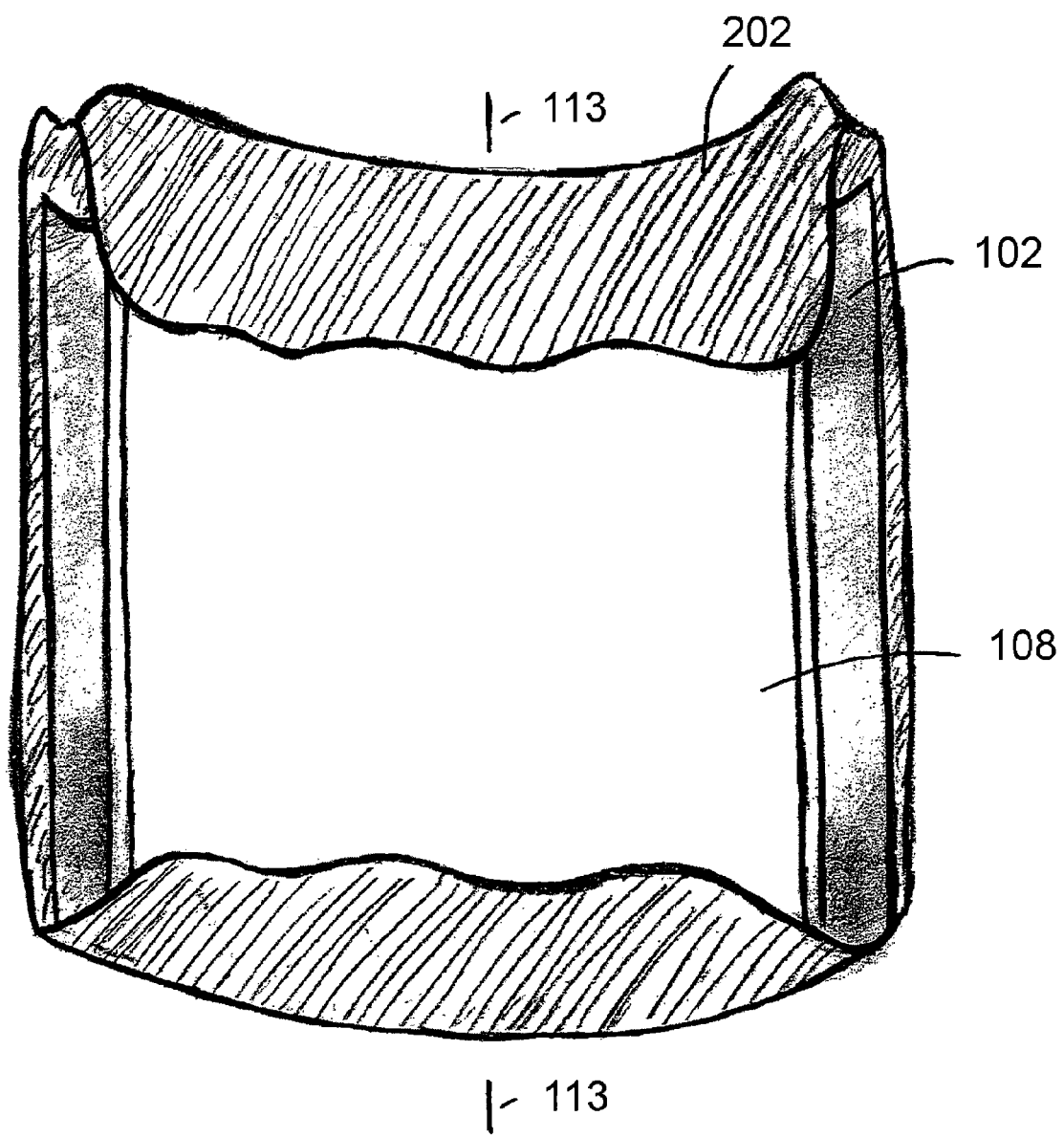
FIG. 2 is an illustration of a wicking structure assembly.

Referring to FIG. 2, a wicking structure assembly 200 includes a wrapper 202 and a wicking structure having an outer wick 102 and an inner wick 108. The wrapper 202 envelops (e.g., encases or surrounds) the wicking structure such that the wrapper 202 forms a barrier between the outer surface of the outer wick 102 and air. In addition, the wrapper 202 is folded over at the two ends of the wicking structure 100 such that the wrapper 202 also encases a portion of the inner wick 108. For example, the wrapper 202 may be folded over at the two ends of the wicking structure such that the wrapper 202 encases approximately 0.5 inches of the inner wick 108 at either end of the wicking structure 100. The wrapper 202 may prevent, or at least limit, fragrance material from evaporating from the outer surface 104 of the outer wick 102. In addition, the folded ends of the wrapper 202 may prevent fragrance material from leaking from the ends of the outer wick 102 and the inner wick 108 of the wicking structure. In one implementation, the wrapper 202 is composed of a polyester film. However, the wrapper 202 may be composed of other materials, including, for example, foil.

In some implementations, the outer wick 102 and the inner wick 108 have different porosities. More particularly, the outer wick 102 is configured to be more porous than the inner wick 108 such that the outer wick 102 does not retain fragrance material as well as the inner wick 108. Stated differently, the outer wick 102 has a tendency to release fragrance material more quickly than the inner wick 108. In addition to impacting the ability of the outer wick 102 and the inner wick 108 to retain fragrance material, the porosities of the outer wick 102 and the inner wick 108 also may influence the capacity of the outer wick 102 and the inner wick 108 for absorbing fragrance material.

The wicking structure is wrapped by the wrapper 202, which creates a barrier between the outer surface 104 of the outer wick 102 and air such that the outer wick 102 is exposed to only the inner wick 108. Consequently, the rate at which the outer wick 102 releases fragrance material may be tempered (e.g., regulated or controlled) by the ability of the inner wick 108 to receive (e.g., absorb) fragrance material from the outer wick 102. If the inner wick 108 is saturated with fragrance material, the inner wick 108 is unable to absorb additional fragrance material, which causes the outer wick 102 to retain the fragrance material until the inner wick 108 is capable of absorbing fragrance material. After the inner wick 108 has reached saturation, the inner wick 108 is unable to absorb fragrance material from the outer wick 102 until after the inner wick 108 has released fragrance material (e.g., until fragrance molecules of the fragrance material have evaporated into the air) so that the inner wick 108 is no longer saturated. Thus, the rate at which the inner wick 108 absorbs fragrance material may be a function of the rate at which the inner wick 108 releases fragrance material.

Absent other mechanisms for releasing fragrance material, the rate at which the inner wick 108 absorbs fragrance material may be a function of the rate at which fragrance molecules are evaporated from the inner surface 112 of the inner wick 108. Consequently, the rate at which the outer wick 102 transfers fragrance material to the inner wick 108 may be a function of the rate at which fragrance molecules are evaporated from the inner surface 112 of the inner wick 108. In this manner, the inner wick 108 may be said to function as a control mechanism for regulating the rate at which the molecules of the fragrance material fed to the inner wick 108 by the outer wick 102 are released into the air.

Other features of the wicking structure also may affect (e.g., regulate) the rate at which the molecules of the fragrance material are released into the air. For example, the outer wick's capacity for retaining fragrance material may influence the rate at which fragrance material is released into the air, as might the rate of migration of fragrance material through the outer wick 102 and/or the inner wick 108. In addition, the placement of barriers on or between the surfaces of the outer wick 102 and/or the inner wick 108 may help to regulate the rate at which fragrance is released.

To achieve wicks of different porosities, the outer wick 102 and the inner wick 108 may be composed of different materials. In some implementations, the outer wick 102 is a felt wick and the inner wick 108 is a blotter paper wick.

In one example of a felt wick, fibers of the felt wick are arranged radially with respect to the axis 113 such that the felt exhibits a grain running from the outer surface of the felt wick to the inner surface of the felt wick. This configuration of fibers may foster the flow of fragrance material within the felt wick. Additionally, it may limit the ability of the felt wick to retain absorbed fragrance material. In order to vary the felt wick's ability to absorb and retain fragrance oil, the density of the fibers (e.g., the denier of the felt) may be varied. Generally, the more tightly the fibers of the felt wick are woven (i.e., the greater the density of the fibers), the greater the capacity of the felt wick for retaining fragrance material. In some implementations, felt wicks may be composed of felt having a denier of 3 to 6.

In one example, the blotter paper wick is composed of a cellulose paper material. In contrast to the example of the felt wick, in some implementations the blotter paper wick may not exhibit a defined grain, although in other implementations the blotter paper wick may exhibit a defined grain or pattern. The blotter paper wick retains absorbed fragrance material more readily than the felt wick. As such, the blotter paper wick may function as a control mechanism for releasing fragrance into the air.

As illustrated in FIGS. 1 and 2, the inner wick 108 is longer than the outer wick 102. However, the inner wick 108 also may be configured to be the same length as, or shorter than, the outer wick 102. In some implementations where the inner wick 108 is shorter than the outer wick 102, the dimensions of the wrapper 202 are configured such that when the wrapper is folded over, the wrapper 202 covers portions of the outer wick 102 that otherwise would be exposed to air. This may help to decrease the likelihood of leakage. Additionally or alternatively, if the inner wick 108 is shorter than the outer wick 102, the amount of fragrance material applied to the outer wick 102 may be controlled so as to diminish the likelihood of leakage.

Figure 3A:
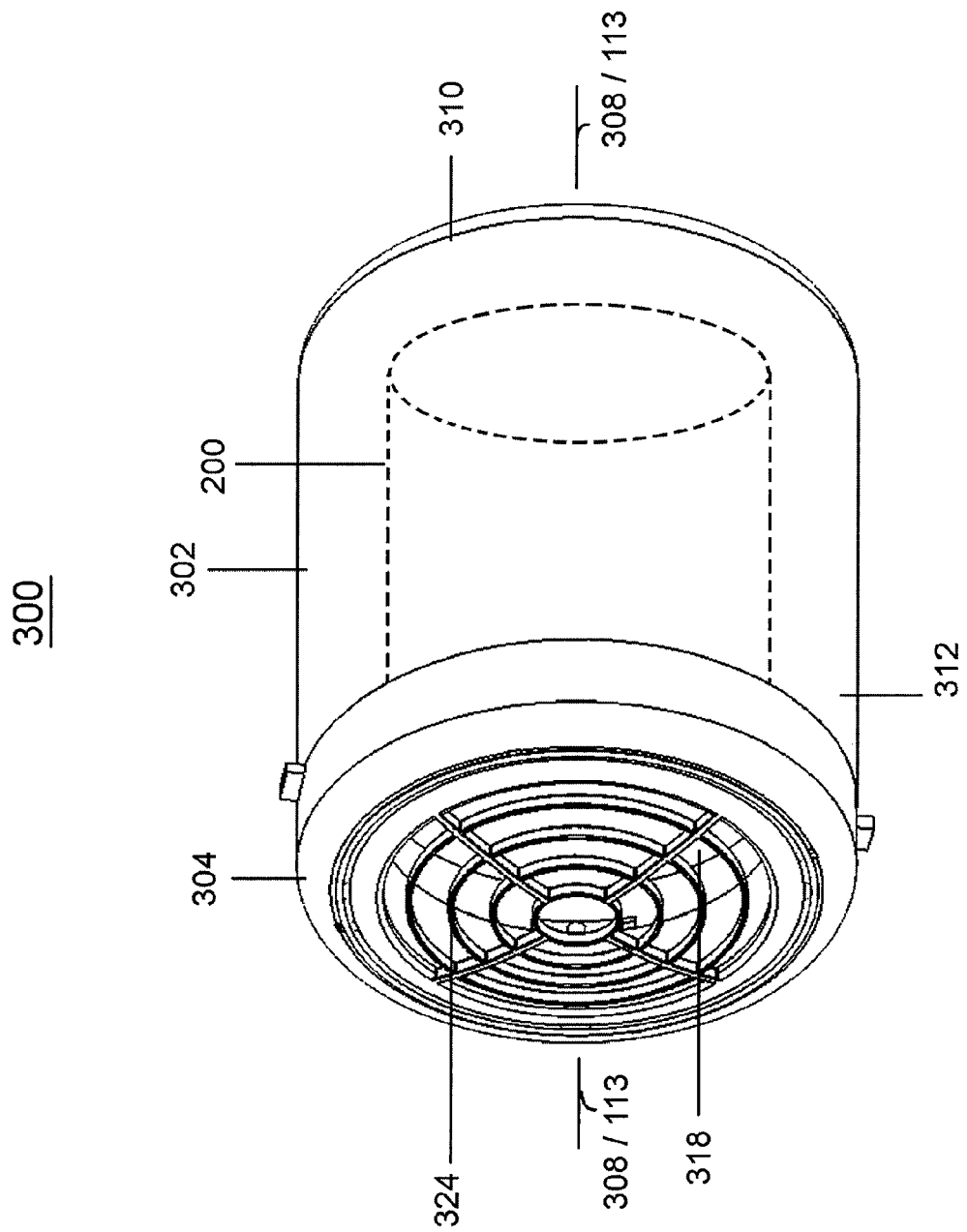
FIGS. 3A and 3B are illustrations of a fragrance dispensing canister assembly.
Figure 3B:
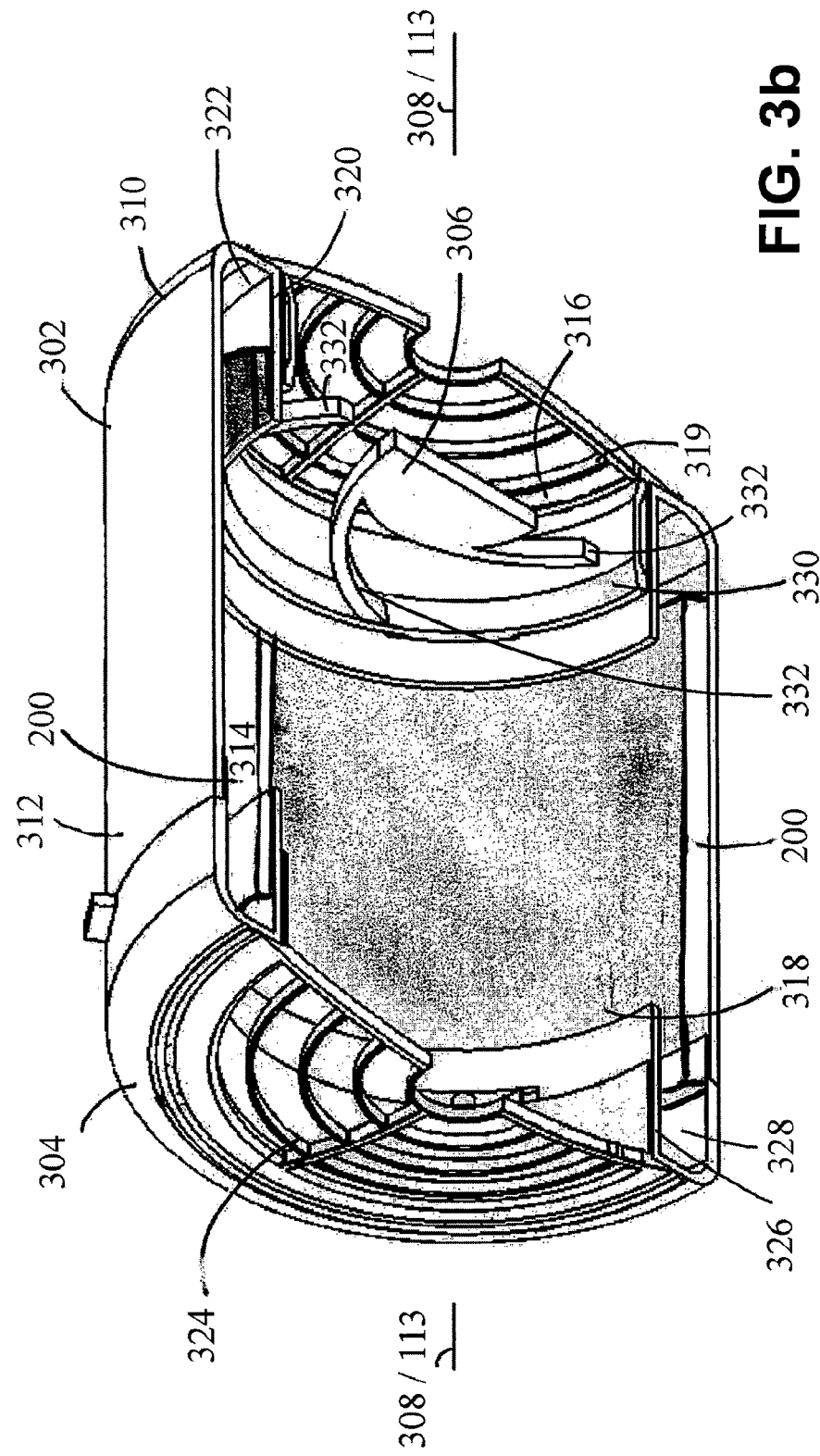

Referring to FIGS. 3A and 3B, a fragrance dispensing canister assembly 300 (e.g., a cartridge) includes a wicking structure assembly 200, a canister body 302, a nose cone 304 (e.g., a lid), and a fan 306. The canister body 302 is configured in the form of a hollow cylinder about an axis 308 and has an air intake end 310 and an air output end 312. The hollow canister body 302 defines a canister interior 314, an air intake aperture 316 located at the air intake end 310 of the canister body 302, and an air output aperture 318 located at the air output end 312 of the canister body 302. The canister body 302 further includes circular grill slats 319 covering the air intake aperture 316. Other configurations also may be used to cover the air intake aperture 316. For example, a mesh grill or louvers may be used to cover the air intake aperture 316. Alternatively, the air intake aperture 316 may be uncovered.

The wicking structure assembly 200 is received within the canister interior 314 such that the outer wick 102 is positioned between the inner wick 108 and the canister body 302 and the wrapper 202 is positioned between the outer wick 102 and the canister body 302. The axis 113 of the wicking structure 100 is aligned with the axis 308 of the canister body 302. Consequently, the wicking structure 100 and the canister body 302 form concentric cylinders such that air may enter the canister interior 314 through the air intake aperture 316, flow through the air channel of the wicking structure 100, and exit the canister interior 314 through the air output aperture 318.

The canister body 302 is further configured to form a lip 320 at the air intake end 310 that wraps around the wicking structure assembly 200. The lip 320 interacts with (e.g., pinches) the folded-over wrapper 202 in order to hold the wrapper 202 in place and form a seal between the folded-over wrapper 202 and the inner surface 112 of the inner wick 108 in the vicinity of the air intake end 310 of the canister body 302. The seal may create a barrier between the outer wick 102 and air. Additionally, the seal may prevent, or at least limit, fragrance material from leaking from the wicking structure assembly 200. The lip 320 also may serve to hold the wicking structure assembly 200 in place within the canister interior 314. Additionally or alternatively, the lip 320 may prevent fragrance material from leaking out of the canister assembly 300 through the air intake aperture 316 by forming a well 322 for collecting fragrance material that leaks from the wicking structure assembly 200. The canister body 302 may be composed of various different materials including, for example, plastic, metal, polyester film, or a combination thereof.

The nose cone 304 is coupled to the air output end 312 of the canister body 302. As illustrated, the nose cone 304 includes circular grill slats 324. The circular grill slats 324 may help to regulate or direct airflow through the air output aperture 318. Other mechanisms also may be used to help regulate or direct airflow through the air output aperture 318. For example, a mesh grill or louvers may be used to regulate airflow through the air output aperture 318.

The nose cone 304 is configured to form a lip 326 that wraps around the wicking structure assembly 200 in the vicinity of the air output end 312 of the canister body 302. Like the lip 320 formed at the air intake end 310 of the canister body 302, the lip 326 interacts with the folded-over wrapper 202 in order to hold the wrapper 202 in place and to form a seal between the folded-over wrapper 202 and the inner surface 112 of the inner wick 108 in the vicinity of the air output end 312 of the canister body 302. The seal may create a barrier between the outer wick 102 and the air. Additionally, the seal may prevent, or at least limit, fragrance material from leaking from the wicking structure assembly 200. The lip 326 may also serve to hold the wicking structure assembly 200 in place within the canister interior 314. Additionally or alternatively, the lip 326 may prevent fragrance material from leaking out of the canister assembly 300 through the air output aperture 318 by forming a well 328 for collecting fragrance material that leaks from the wicking structure assembly 200.

The fan 306 includes a fan housing 330 and fan blades 332 and is coupled to the canister body 302 in the vicinity of the air intake end 310. The fan 306 is configured to encourage airflow through the air channel and to project air out of the canister assembly 300. During operation, the fan 306 forces airflow through the air channel by drawing air into the air channel through the air intake aperture 316 and propelling air out of the air channel through the air output aperture 318.

The fan blades 332 are aligned substantially with the inner surface 112 of the inner wick 108. Stated differently, the fan blades 332 and the air channel are configured to have substantially the same dimensions. Configuring the fan blades 332 such that they are of substantially the same dimension as the air channel may increase the efficiency of the fan 306 as substantially all of the airflow generated by the fan may be corralled within the air channel thereby eliminating, or at least reducing, blow-by. Configuring the fan blades 332 such that they are of substantially the same dimension as the air channel also may limit the amount of noise generated by the fan 306 during operation.

The fan 306 may be equipped with a power supply. Alternatively or additionally, the fan 306 may be configured to receive power from an external source.

Using the fan 306 to force airflow through the air channel helps to increase the rate of evaporation of fragrance molecules from the wicking structure 100. In general, as the velocity of the airflow through the air channel increases, the evaporation rate of the fragrance molecules also increases. Additionally, using the fan 306 to propel air out of the air channel helps the canister assembly 300 to disperse fragrance molecules across a larger volume than otherwise would occur.

A fragrance dispensing canister assembly having an outer wick and inner wick of a wicking structure as described previously may provide advantages, particularly in an industrial or retail environment, over other methods of fragrance diffusion, such as an aerosol atomizer or a conventional automatic scent diffusing mechanism that is designed to sit on top of a desk to diffuse fragrance into an office space, or plug into a wall socket to diffuse fragrance in the surrounding area. For example, fragrance potency may be supplied to a relatively large commercial space.

Figure 4:
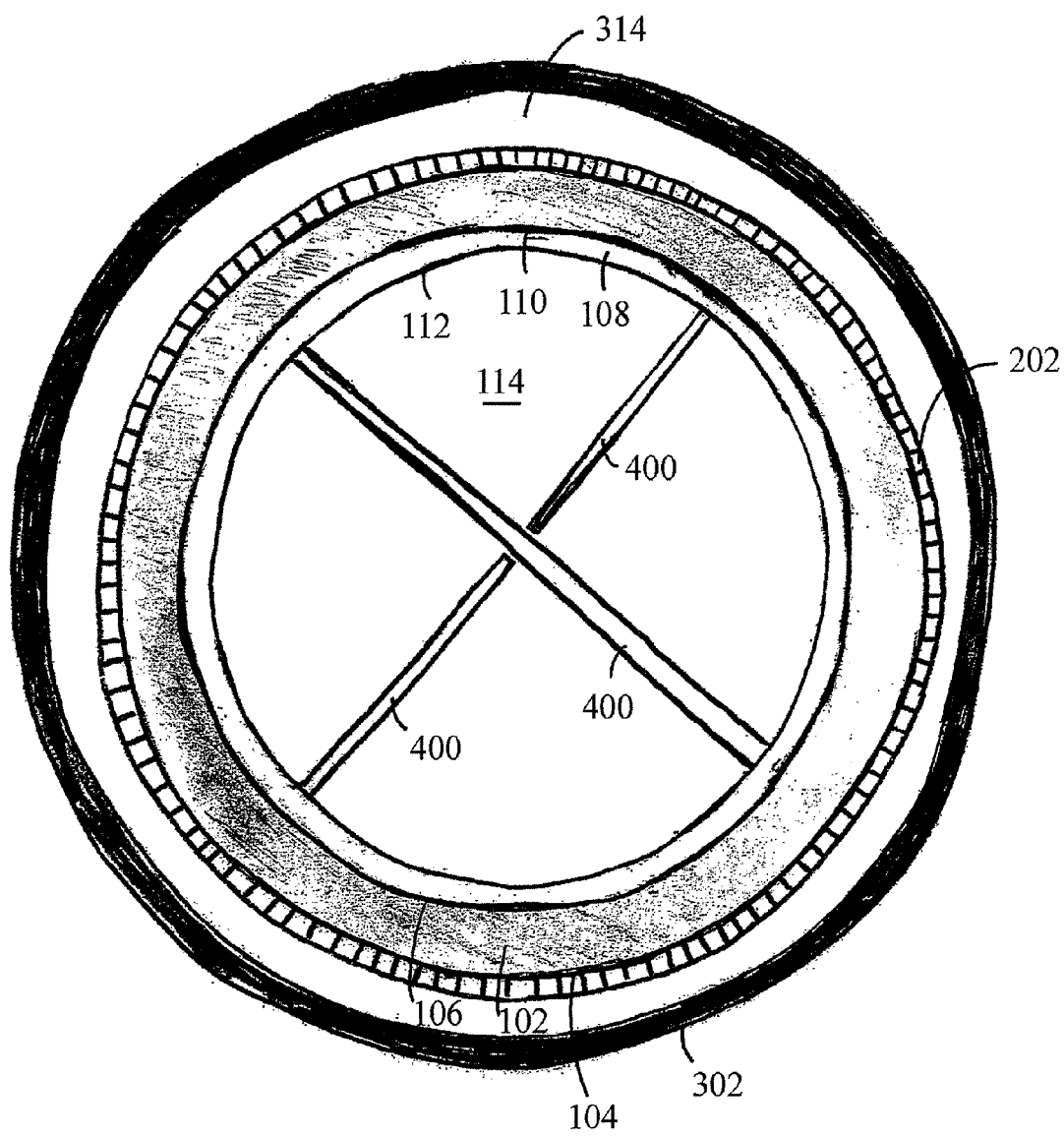
FIG. 4 is a cross sectional view of a portion of a fragrance dispensing canister assembly.

Referring to FIG. 4, in some implementations, air channel dividers 400 are positioned within the air channel. In order to prevent the air channel dividers 400 from slipping or otherwise moving within the air channel, the air channel dividers 400 may be secured to or integrated within the wicking structure. Additionally or alternatively, the air channel dividers 400 may rest on the inner surface 112 of the inner wick 108 such that the air channel dividers 400 are held in place by friction between the air channel dividers 400 and the inner surface 112 of the inner wick 108.

The air channel dividers 400 may be of substantially the same length as the wicking structure 100 and may segment the air channel into separate channels. As a result, the air channel dividers 400 may produce a more linear airflow. During operation, the rotation of the fan blades 332 may throw air off of the fan blades 332 in a circular or spiraling fashion resulting in a circular or spiraling airflow. However, the air channel dividers 400 may catch the air thrown off of the fan blades 332 and force the air to flow more linearly through the segmented channels.

In the example of FIG. 4, the air channel dividers 400 are positioned such that they contact the inner surface 112 of the inner wick 108. In some implementations, the airflow dividers 400 may be capable of absorbing fragrance material. For example, the air channel dividers 400 may be composed of the same or substantially similar material as the inner wick 108. Consequently, fragrance material may be drawn into the air channel dividers 400 from the inner surface 112 of the inner wick 108. As a result, the air channel dividers 400 may provide additional surface area for exposing fragrance molecules to air within the air channel, which, in turn, results in the transfer of more fragrance molecules to the air and a disbursement of a stronger fragrance. In some implementations, notches may be cut through the inner wick 108 so as to allow the air channel dividers 400 to contact the inner surface 106 of the outer wick 102. Allowing the air channel dividers 400 to contact the inner surface 106 of the outer wick 102 may allow the air channel dividers 400 to absorb more fragrance material than the air channel dividers 400 otherwise would absorb by contacting the inner surface 112 of the inner wick 108.

Additionally or alternatively, in order to produce a more linear airflow through the air channel without simultaneously increasing the surface area for exposing fragrance molecules to the air, the air channel dividers 400 may be composed of material that does not absorb fragrance material readily such as, for example, non-porous plastic or metal. Moreover, in some implementations, the air channel dividers 400 may not contact the inner surface 112 of the inner wick 108.

As illustrated in FIG. 4, the air channel dividers 400 form a cross or wagon-wheel pattern. However, other configurations are, possible. For example, the air channel dividers 400 may be configured to form patterns such as zigzags, curlyqueues, or squares. In addition, fewer than three, or more than three, air channel dividers may be positioned within the air channel.

Figure 5A:
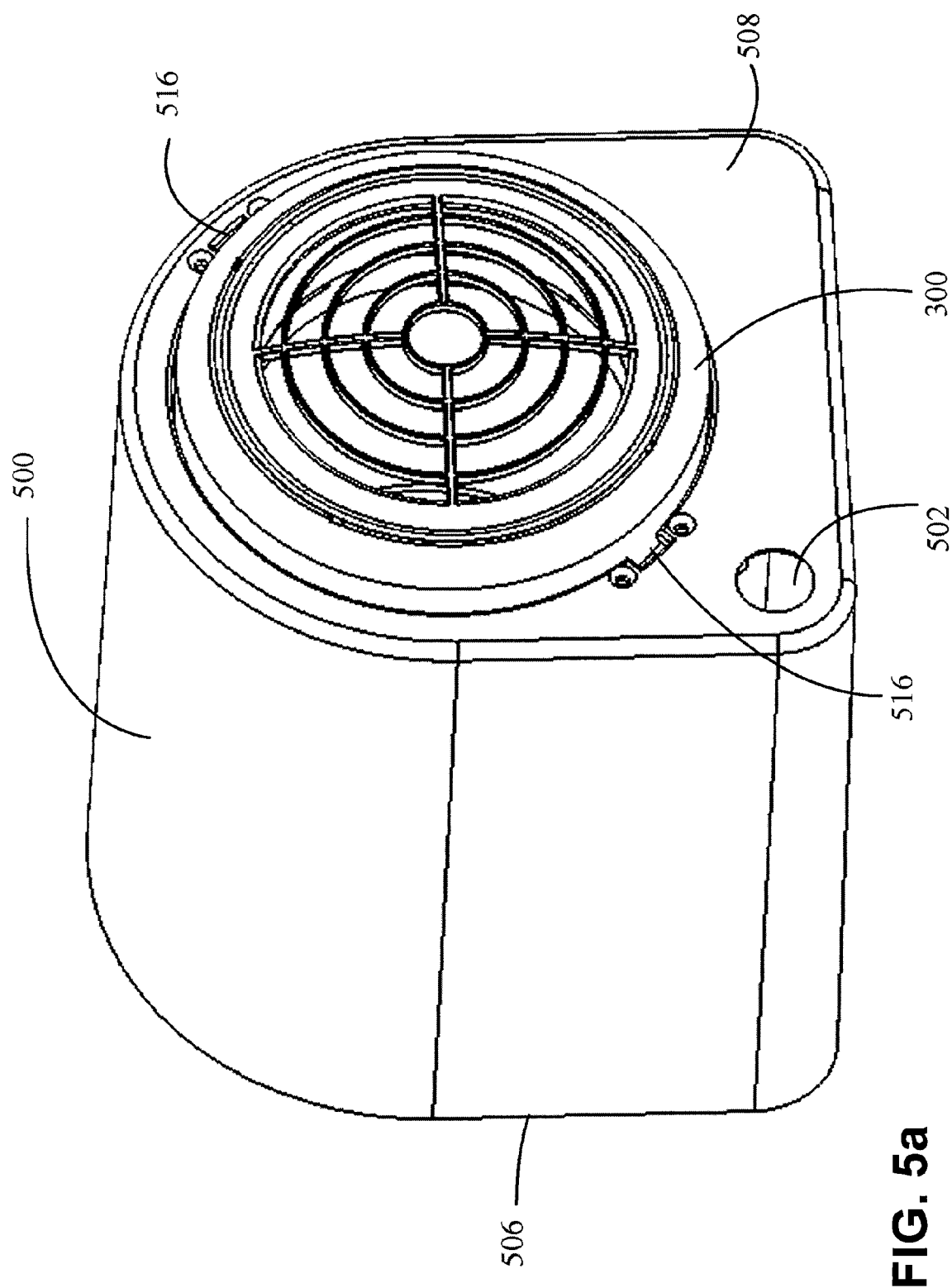
FIG. 5A is an illustration of a canister housing with a fragrance dispensing canister assembly.
Figure 5B:
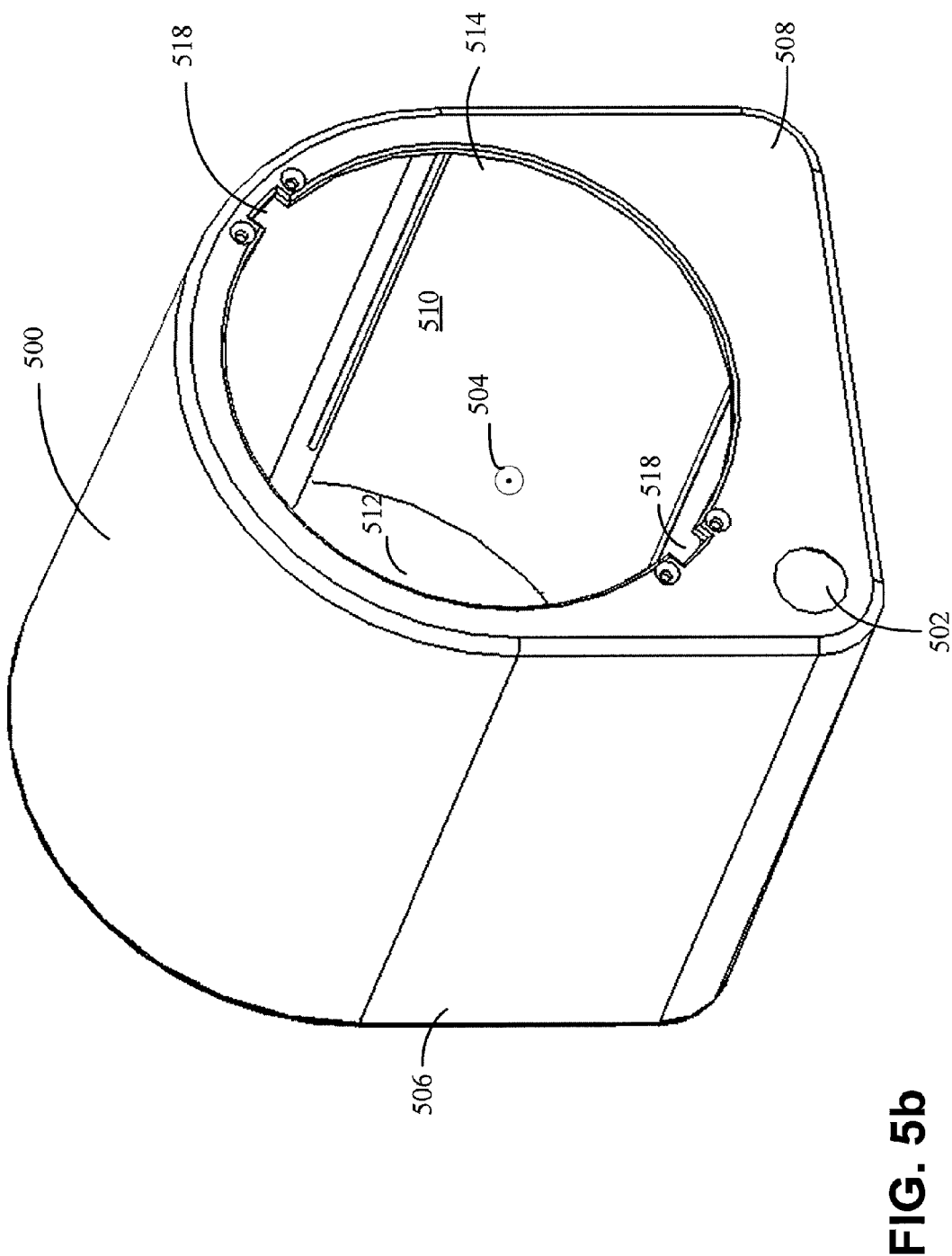
FIG. 5B is an illustration of a canister housing.

Referring to FIGS. 5A and 5B, the fragrance releasing canister assembly 300 is housed in a canister housing 500 having a motion sensor 502 and an electrical outlet 504 for providing power to the fan 306 of the canister assembly 300. The canister housing 500 also includes a housing intake end 506 and a housing output end 508. In addition, the canister housing 500 defines a canister cavity 510 configured to receive the canister assembly 300, a housing intake aperture 512 leading to the canister cavity 510 at the housing intake end 506, and a housing output aperture 514 leading to the canister cavity 510 at the housing output end 508. The canister assembly 300 is received within the canister cavity 510 with the air intake end 310 of the canister body 302 positioned in the vicinity of the housing intake end 506 and the air output end 312 of the canister body 302 positioned in the vicinity of the housing output end 508.

The canister housing 500 may be equipped with a power supply capable of supplying power, such as a battery assembly. Additionally or alternatively, the canister housing 500 may be equipped to receive power from an external source.

The canister housing 500 may be configured to regulate the power (e.g., voltage or current) supplied to the fan, thereby allowing the fan speed to be controlled. In some implementations, the canister housing 500 includes controls for manually setting (e.g., selecting or controlling) the fan speed. Manually setting the fan speed enables a person to adjust the amount of fragrance dispensed. For example, selecting a higher fan speed causes more air to flow through the canister, which results in more fragrance being dispensed. In contrast, selecting a lower fan speed or turning off the fan causes less air to flow through the canister (as compared with a higher fan speed), which results in less fragrance being dispensed. Other mechanisms for regulating the airflow through the air channel also may be employed. For example, moveable partitions for closing, or partially closing, the air intake aperture 316 and/or the air output aperture 318 may be incorporated into the canister assembly 300.

The motion sensor 502 may be configured to detect motion up to a predetermined distance, such as twenty feet away from the motion sensor 502.

The power supplied to the fan 306 also may be controlled at least in part by the motion sensor 502. Consequently, the operation of the fan 306 also may be controlled by the motion sensor 502. For example, power may be supplied to the fan when the motion sensor 502 detects motion within the vicinity of the canister housing 502. The canister housing 500 also may include a timing circuit for regulating the power provided to the fan 306. The timing circuit may control the power provided to the fan 306 such that the fan 306 is cycled on and off. For example, the fan 306 may be cycled on for 30 seconds and off for 30 seconds. The period of the cycle may be variable. The timing circuit also may be configured to operate in conjunction with the motion sensor 502. For example, the timing circuit may be triggered to provide power to the fan 306 in response to the detection of motion by the motion sensor 502. The timing circuit then may cut off the supply of power to the fan 306 after a defined period of time has elapsed since the detection of motion.

As such, the canister housing 500 is operable to deliver fragrance when the motion sensor 502 is triggered and may be referred to as a sensing fragrance apparatus. Thus, a sensing fragrance apparatus provides for the diffusion of fragrance when a person is believed to be present in an environment, such as when motion is detected or a person otherwise makes his/her presence known (e.g., logs into a computer to authenticate to a security system) or where a sensor detects indicia of presence by one or more people (e.g., motion, pattern recognition, and sound changes, levels or characteristics are detected). In this way, a sensing fragrance apparatus may provide the effect of a continuous fragrance dispensing system when people are present in the environment, while saving on the amount of costly fragrance oil and energy otherwise consumed. Other examples of the types of sensors that may be included in the sensing fragrance apparatus include a light sensor, a heat sensor, a tactile or haptic sensor, and an ultrasonic sensor. In addition, a wireless receiver may be included in, or with, a sensing fragrance apparatus to enable remote control of the diffusion of fragrance.

Other conditions also may be used to trigger diffusion or disbursement of fragrance. For example, a door opening or closing at a store entrance may be detected and trigger diffusion of fragrance. Passage of a predetermined time interval or specific intervals of time also may trigger diffusion of fragrance. For example, fragrance may begin diffusing in the morning when a retail store opens and stop diffusing in the evening when the retail store closes. In addition, different fragrances may be diffused based on the occurrence of different conditions. In one example, a fragrance may be diffused in the morning, and a different fragrance may be diffused in the evening. In order to diffuse different fragrances, two canister assemblies, each including a wicking structure impregnated with a different fragrance, may be housed in a single canister housing. Other environmental cues also may be used to trigger disbursement of fragrance, such as detection of presence or absence of sunlight and/or presence or absence of heat.

Voice recognition and sound detection also may be used to activate or deactivate the release of a fragrance or a particular fragrance. For example, a specific voice command may trigger the diffusion of a fragrance or a particular fragrance, whereas a different voice command may stop the diffusion of the fragrance or the particular fragrance.

Referring again to FIGS. 5a and 5b, the canister housing 500 may be configured to allow the canister housing 500 to be mounted to a structure or fixture. For example, the canister housing 500 may be mounted on a wall or installed in a standard lighting fixture.

When mounted, the canister housing 500 may be aimed at a particular space to provide the necessary potency of fragrance for a short duration for a targeted location, rather than continuous operation for diffusion of fragrance. When a person approaches the targeted area near the canister housing, the motion sensor 502 triggers the fan to blow for a specified period of time, which diffuses fragrance into the environment. Thus, the canister housing 500 may help to provide the effect of a continuous fragrance dispensing system in the targeted area, while reducing the amount of fragrance oil used because the fragrance dispensing apparatus only operates when a trigger condition (here, motion) is detected in the targeted area.

The canister housing 500 may be configured further to allow the canister assembly 300 to be removed from the canister housing 500. Thus, after a portion of the fragrance material in the canister assembly 300 has evaporated from the wicking structure 100, the canister assembly 300 may be removed and replaced with a new canister assembly having a full complement of fragrance material.

Referring to FIGS. 5a and 5b, in some implementations, a quick-mount canister assembly 300 replacement may be used. The canister housing 500 defines grooves 518 for receiving locking tabs 516 coupled to the nose cone 304 of the canister assembly 300 thereby enabling the canister assembly 300 (or cartridge) to be inserted into the canister housing 500 and rotated clockwise to secure.

Once the fragrance in the canister assembly is depleted, nearly depleted, or a predetermined passage of time has occurred, the canister assembly may be replaced with a new canister assembly, for example, by using a simple twisting action to unlock and remove the canister assembly. A canister assembly also may be replaced to change to a different fragrance.

In an example of use in a retail store, each department area of the store may be "scent zoned" by a fragrance dispensing apparatus. This may provide the retailer the opportunity to choose specific fragrances for each zone. For example, a department store could have a fresh linen fragrance for the bedding section, a leather fragrance for the men's shoes section, and a waffle cone fragrance for the children's toys section.

EXAMPLE 1

In one example of a fragrance dispensing apparatus, the canister assembly has the following dimensions:
Evaporative surface area . . . 110" squared
Wicking agent reservoir volume . . . 38" cubed
Reservoir contact surface area . . . 51" squared Wicking surface area . . . . 51" squared The evaporative control surface area represents the surface area of the inner surface 112 of the inner wick 108 and the surface area of the air channel dividers 400. The wicking agent reservoir volume represents the volume of the outer wick 102. The reservoir contact surface area represents the surface area of the inner surface 106 of the outer wick 102. Lastly, the wicking surface area represents the outer surface 110 of the inner wick 108.

The canister housing includes a 12 volt fan with an airflow capability of 20 cubic feet per minute. The fragrance oil used in the example canister assembly may have an eight percent efficiency over a thirty day life. In addition, the fragrance dispensing apparatus may provide fragrance potency to a 40,000 cubic foot space.

EXAMPLE 2

A fragrance dispensing apparatus may be ceiling mounted by attaching the canister housing to mounting tracks (which may be referred to as track-mounting). These mounting tracks may be sufficiently sturdy to mount the canister housing and provide enough electrical power to operate the fragrance dispensing apparatus. This may help to avoid some types of the electrical cabling, cosmetic, and mounting issues. In some cases, commercial spaces may be pre-equipped with mounting tracks, which may further reduce the costs of installation, cabling, and mounting of the fragrance dispensing apparatus. In addition, attaching the canister to mounting tracking may allow the canister housing to be moved among various different positions along the tracking.

In some implementations, the aesthetic appearance of the fragrance dispensing apparatus may be important. In such a case, the design of the fragrance dispensing apparatus may be optimized to "blend in" with the current lighting in place. This may be achieved by an adjustable angle, color, and lamp type shape. The sensing fragrance machine may be installed into a standard lighting fixture, for example, a Halo or Juno lighting fixture.

A fragrance dispersing apparatus may diffuse a particular fragrance based on a particular environmental cue to supplant or supplement one or more senses of a person. For example, a particular fragrance may be released to cue a blind and/or hearing-impaired individual to an environmental condition, such as a ringing telephone, a doorbell, or the existence of an emergency condition. In one implementation, the fragrance dispersing apparatus is coupled to a telephone such that an incoming signal indicating an incoming call causes the telephone to ring and simultaneously triggers the fragrance dispersing apparatus to release fragrance. In another implementation, the fragrance dispersing apparatus is coupled to a doorbell such that depressing the doorbell causes the doorbell to ring and simultaneously triggers the fragrance dispersing apparatus to release fragrance. In still another implementation, the fragrance dispersing apparatus is coupled to a fire alarm such that pulling the fire alarm causes a siren to ring and simultaneously triggers the fragrance dispersing apparatus to release fragrance.

Figure 6:
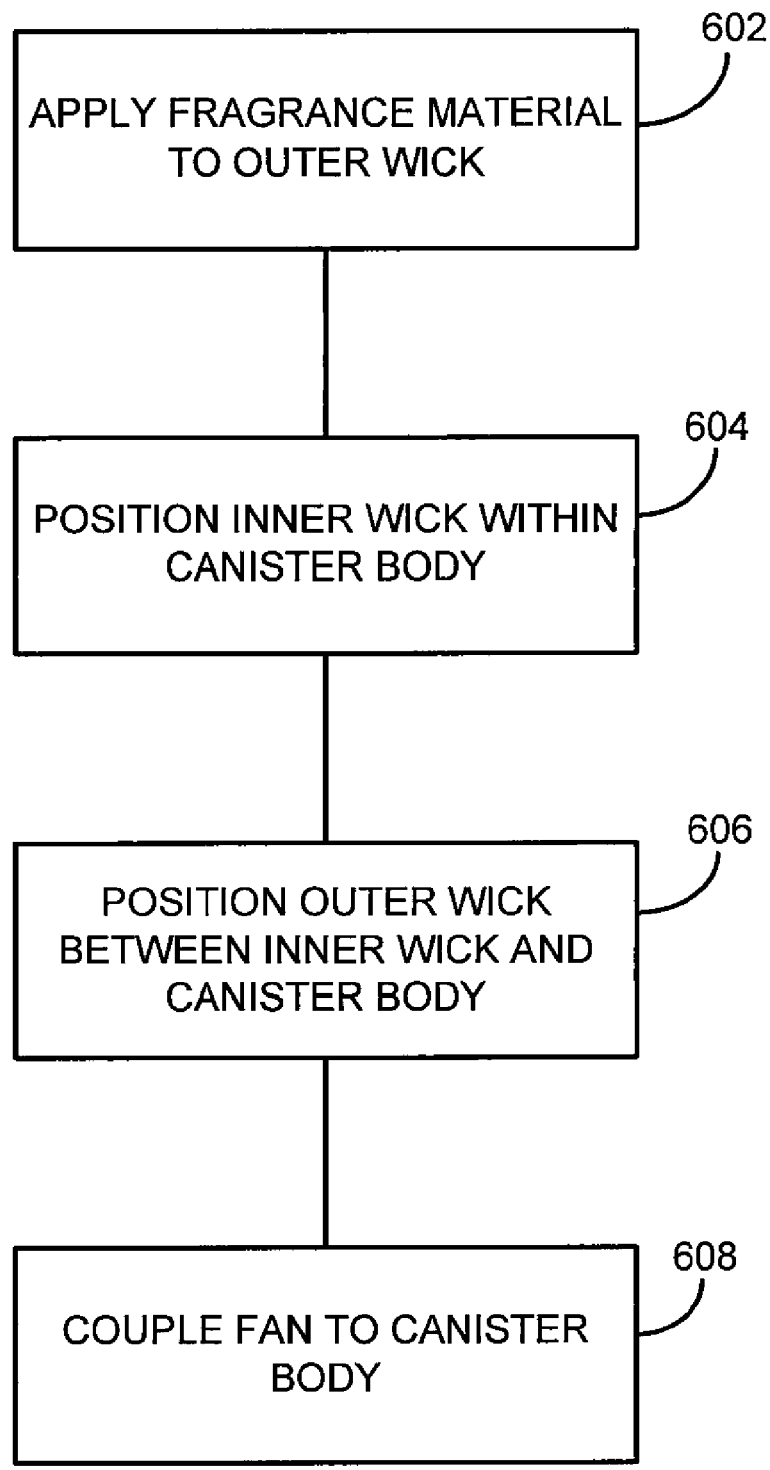
FIG. 6 is a flowchart of a process for assembling a canister.

Referring to FIG. 6, a process 600 for assembling a canister for releasing fragrance material is illustrated. The canister includes an inner wick, an outer wick, a canister body, and a fan. Fragrance material is applied to the outer wick (operation 602). The inner wick is positioned within the canister body (operation 604) and the outer wick is positioned between the inner wick and the canister body (operation 606). In addition, the fan is coupled to the canister body (operation 608).

A number of implementations have been described. Nevertheless, it will be understood that various modifications may be made. For example, the canister assembly may be housed in various different types of housing structures including, for example, a heating, ventilation, and air-conditioning (HVAC) duct. Alternatively, the canister assembly may function as a standalone unit, independent of any housing structure.

Similarly, the wicking structure assembly may be received in various different types and shapes of canisters. Alternatively, the wicking structure assembly may function as a standalone unit, independent of any canister structure.

Figure 7:
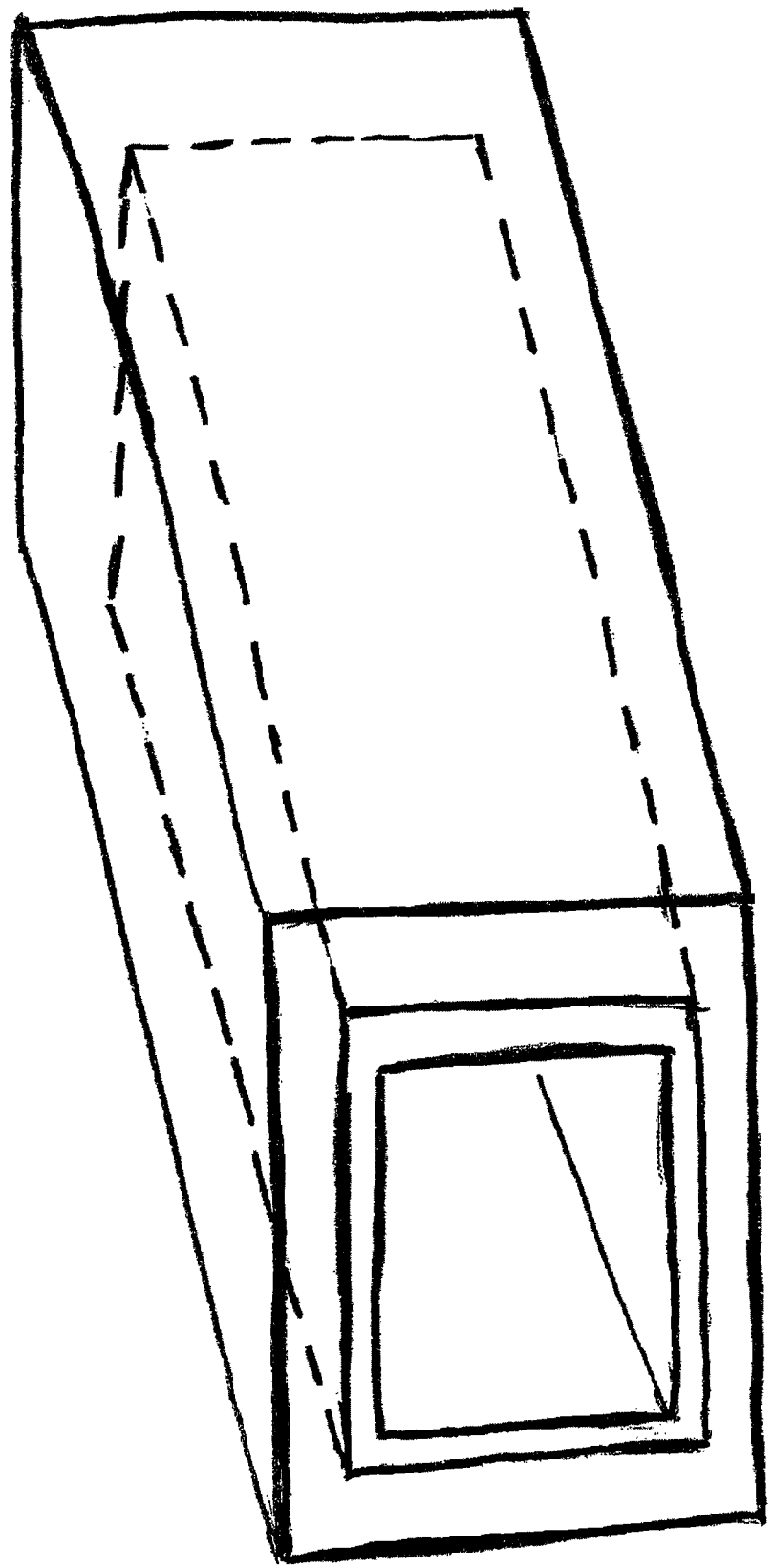
FIG. 7 is an illustration of a wicking structure.

In addition, the wicking structure may be implemented with an integrated wick. The integrated wick may be configured to have an outer portion and an inner portion such that the porosity of the outer portion of the integrated wick is greater than the porosity of the inner portion of the integrated wick. For example, the wicking structure may be composed of a single piece of porous plastic, the porous plastic being configured such that an outer portion of the wick is more porous than an inner portion of the wick. Also, the wicking structure may be configured in numerous different tubular shapes. For example, referring to FIG. 7, the wicking structure may be configured in a substantially rectangular shape.

Additionally, the wicking structure need not be wrapped by a wrapper. For example, the canister assembly may be configured so as to create a barrier between air and the outer surface of the wicking structure. Additionally or alternatively, the wicking structure may be wrapped only partially.

Furthermore, the fan may be coupled to the canister assembly at the air output end of the canister assembly. Alternatively, the fin may be integrated within the canister body or provided by the canister housing. In some implementations, no fan is provided. Moreover, different mechanisms may be used for encouraging airflow through the air channel in addition to, or in place of the, fan. For example, a compressed air assembly may be used to encourage airflow through the air channel.

While using a fan to encourage airflow through the air channel may increase the rate of evaporation of fragrance material, other techniques for increasing the rate of evaporation of fragrance material also may be employed. For example, the wicking structure or the canister may be heated to increase the rate of evaporation.

Accordingly, other implementations are within the scope of the following claims.

The invention claimed is:

1. A canister assembly comprising:
   a canister body;
   an inner wick formed from blotter paper positioned within the canister body and configured to define an air passage; and
   an outer wick formed from felt, at least a portion of the outer wick being positioned between the inner wick and the canister body, the inner wick and the outer wick being oriented to enable a transfer of fragrance material to the inner wick from the outer wick, the fragrance material including fragrance molecules, the inner wick being configured to enable a transfer of some of the fragrance molecules into air within the air passage.

2. The canister assembly of claim 1 wherein the outer wick has a greater tendency to transfer the fragrance material than the inner wick.

3. The canister assembly of claim 1 wherein the inner wick and the outer wick form substantially concentric cylinders.

4. The canister assembly of claim 1 wherein the outer wick has an outer surface, the canister assembly further comprising:
   a wrapper, at least a portion of the wrapper being positioned between the outer wick and the canister body, wherein the wrapper encases at least a portion of the outer surface of the outer wick.

5. The canister assembly of claim 4 further comprising:
   a lip, wherein the lip interacts with the wrapper to form a seal between the wrapper and an inner surface of the inner wick.

6. The canister assembly of claim 1 further comprising:
   a lip for collecting excess fragrance material.

7. The canister assembly of claim 1 wherein the fragrance material comprises fragrance oil.

8. The canister assembly of claim 1 wherein:
   the inner wick and the outer wick form an integrated wick,
   the inner wick comprises an inner portion of the integrated wick,
   the outer wick comprises an outer portion of the integrated wick, and
   the outer portion of the integrated wick is more porous than the inner portion of the integrated wick.

9. The canister assembly of claim 1 wherein felt of the outer wick has a denier within a range of 3-6.

10. The canister assembly of claim 1 wherein:
    the outer wick has an inner surface positioned adjacent to the inner wick and an outer surface positioned opposite the inner surface; and
    fibers of the felt of the outer wick are arranged to provide a grain within the outer wick that runs between the outer surface and the inner surface of the outer wick.

11. A canister assembly comprising:
    a canister body;
    an inner wick positioned within the canister body and configured to define an air passage; and
    an outer wick having an outer surface, at least a portion of the outer wick being positioned between the inner wick and the canister body, the inner wick and the outer wick being oriented to enable a transfer of fragrance material to the inner wick from the outer wick, the fragrance material including fragrance molecules, the inner wick being configured to enable a transfer of some of the fragrance molecules into air within the air passage;
    a wrapper, at least a portion of the wrapper being positioned between the outer wick and the canister body, wherein the wrapper encases at least a portion of the outer surface of the outer wick; and
    a lip, wherein the lip interacts with the wrapper to form a seal between the wrapper and an inner surface of the inner wick.

12. A canister assembly comprising:
    a canister body;
    an inner wick positioned within the canister body and configured to define an air passage;
    an outer wick, at least a portion of the outer wick being positioned between the inner wick and the canister body, the inner wick and the outer wick being oriented to enable a transfer of fragrance material to the inner wick from the outer wick, the fragrance material including fragrance molecules, the inner wick being configured to enable a transfer of some of the fragrance molecules into air within the air passage; and
    a lip for collecting excess fragrance material.

13. A canister assembly comprising:
    a canister body;
    an inner wick formed from blotter paper positioned within the canister body and configured to define an air passage; and
    an outer wick formed from a woven fibrous material that differs from the inner wick, at least a portion of the outer wick being positioned between the inner wick and the canister body, the inner wick and the outer wick being oriented to enable a transfer of fragrance material to the inner wick from the outer wick, the fragrance material including fragrance molecules, the inner wick being configured to enable a transfer of some of the fragrance molecules into air within the air passage.

14. The canister assembly of claim 13 wherein the woven fibrous material of the outer wick has a denier within a range of 3-6.

15. The canister assembly of claim 13 wherein the woven fibrous material of the outer wick comprises felt.

16. The canister assembly of claim 13 wherein the woven fibrous material of the outer wick comprises felt having a denier with a range of 3-6.

17. The canister assembly of claim 13 wherein:
    the outer wick has an inner surface positioned adjacent to the inner wick and an outer surface positioned opposite the inner surface; and
    fibers of the fibrous material are arranged to provide a grain within the outer wick that runs between the outer surface and the inner surface of the outer wick.

* * * * *

UNITED STATES PATENT AND TRADEMARK OFFICE
CERTIFICATE OF CORRECTION

| | | |
|---|---|---|
| PATENT NO. | : 7,651,077 B1 | Page 1 of 1 |
| APPLICATION NO. | : 11/277021 | |
| DATED | : January 26, 2010 | |
| INVENTOR(S) | : Rosener et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 829 days.

Signed and Sealed this

Twenty-eighth Day of December, 2010

David J. Kappos
*Director of the United States Patent and Trademark Office*